United States Patent [19]

Fuchs et al.

[11] 4,233,293

[45] Nov. 11, 1980

[54] INSECTICIDAL AND ACARICIDAL O-ALKYL-O-[1-(2-CYANOALKYL)-5-HALO-1,2,4-TRIAZOL(3)YL]-(THIONO)(THIOL)-PHOSPHORIC(PHOSPHONIC) ACID ESTERS AND ESTER-AMIDES

[75] Inventors: Rainer A. Fuchs, Wuppertal; Ingeborg Hammann, Cologne; Wolfgang Behrenz, Overath-Steinenbrueck, all of Fed. Rep. of Germany

[73] Assignee: Bayer Aktiengesellschaft, Leverkusen, Fed. Rep. of Germany

[21] Appl. No.: 680,408

[22] Filed: Apr. 26, 1976

[30] Foreign Application Priority Data

May 14, 1975 [DE] Fed. Rep. of Germany ....... 2521400

[51] Int. Cl.³ .................... A01N 57/16; A01N 57/32; C07F 9/65
[52] U.S. Cl. .................... 424/200; 548/118; 548/263; 260/465.5 R; 260/959; 260/960
[58] Field of Search .................... 260/308 R; 424/200; 548/118

[56] References Cited

U.S. PATENT DOCUMENTS

| | | | |
|---|---|---|---|
| 3,809,701 | 5/1974 | Dawes et al. | 260/308 R |
| 3,867,396 | 2/1975 | Dawes et al. | 260/308 R |
| 4,081,535 | 3/1978 | Fuchs et al. | 548/118 |
| 4,172,080 | 10/1979 | Dawes et al. | 548/118 |

FOREIGN PATENT DOCUMENTS 2457147 6/1975 Fed. Rep. of Germany.
2253756 7/1975 France.

*Primary Examiner*—Alton D. Rollins
*Attorney, Agent, or Firm*—Sprung, Felfe, Horn, Lynch & Kramer

[57] ABSTRACT

O-Alkyl-O-[1-(2-cyanoalkyl)-5-halo-1,2,4-triazol(3)yl]-(thiono)(thiol)-phosphoric(phosphonic) acid esters and ester-amides of the formula $$\begin{array}{c} RO \diagdown \overset{X}{\underset{\parallel}{P}} - O - \overset{N}{\underset{N-N-CH_2-CH-CN}{\diagup}} \overset{Hal}{\underset{R_2}{\diagdown}} \end{array} \quad (I)$$

in which
R is alkyl with 1 to 6 carbon atoms,
$R_1$ is phenyl or alkyl, alkoxy, alkylthio, monoalkylamino or dialkylamino with 1 to 6 carbon atoms per alkyl or alkoxy,
$R_2$ is hydrogen or alkyl with 1 to 4 carbon atoms,
Hal is halogen, and
X is oxygen or sulfur, which possess insecticidal and acaricidal properties.

3 Claims, No Drawings

INSECTICIDAL AND ACARICIDAL O-ALKYL-O-[1-(2-CYANOALKYL)-5-HALO-1,2,4-TRIAZOL(3)YL]-(THIONO)(THIOL)-PHOSPHORIC(PHOSPHONIC) ACID ESTERS AND ESTER-AMIDES

The present invention relates to and has for its objects the provision of particular new O-alkyl-O-[1-(2-cyanoalkyl)-5-halo-1,2,4-triazol(3)yl]-(thiono)(thiol)-phosphoric (phosphonic) acid esters and ester-amides, which possess insecticidal or acaricidal properties, active compositions in the form of mixtures of such compounds with solid and liquid dipersible carrier vehicles, and methods for producing such compounds and for using such compounds in a new way especially for combating pests, e.g. insects and acarids, with other and further objects becoming apparent from a study of the within specification and accompanying examples.

It is known from German Published Specifications DOS Nos. 2,259,960 and 2,260,015 that O-triazolyl(thiono)phosphoric(phosphonic) acid esters, for example O,O-dimethyl-O-[1-methyl-5-methylthio-1,2,4-triazol(-3)yl]-thionophosphoric acid ester (Compound A), O-ethyl-O-[1-isopropyl-5-methylthio-1,2,4-triazol(3)yl]-thionophenylphosphonic acid ester (Compound B) and O,O-diethyl-O-[1-isopropyl-5-chloro-1,2,4-triazol(3)yl]-thionophosphoric acid ester (Compound C) possess insecticidal and acaricidal properties.

The present invention provides O-triazolyl(thiono)(thiol)-phosphoric(phosphonic) acid esters and ester-amides of the general formula

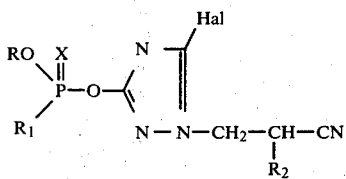

in which
R is alkyl with 1 to 6 carbon atoms,
$R_1$ is phenyl or alkyl, alkoxy, alkylthio, monoalkylamino or dialkylamino with 1 to 6 carbon atoms per alkyl or alkoxy,
$R_2$ is hydrogen or alkyl with 1 to 4 carbon atoms,
Hal is halogen, and
X is oxygen or sulfur, Preferably, R is straight-chain or branched alkyl with 1 to 4, expecially 1 to 3, carbon atoms, $R_1$ is phenyl or straight-chain or branched alkoxy, alkylthio or monoalkylamino each with 1 to 4, especially 1 to 3, carbon atoms, $R_2$ is hydrogen or methyl, Hal is chlorine and X is sulfur.

Surprisingly, the O-triazolyl(thiono)(thiol)-phosphoric(phosphonic) acid esters and ester-amides according to the invention exhibit a better insecticidal and acaricidal action than the compounds of analogous structure and of the same type of action previously known in the art. Accordingly, they represent a genuine enrichment of the art.

The present invention also provides a process for the production of an O-triazolyl(thiono)(thiol)-phosphoric(phosphonic) acid ester or ester-amide of the formula (I) in which a (thiono)(thiol)-phosphoric(phosphonic) acid ester halide or ester-amide halide, respectively, of the general formula

in which
R, $R_1$ and X have the above-mentioned meanings and
$Hal_1$ denotes halogen, preferably chlorine,
is reacted with a triazole derivative of the formula

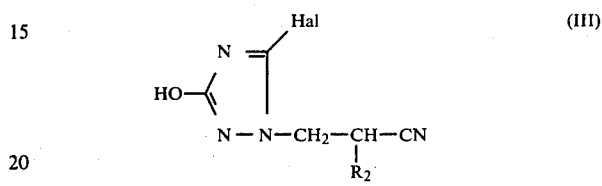

in which $R_2$ and Hal have the above-mentioned meanings, in the presence of an acid acceptor or in the form of an alkali metal salt, alkaline earth metal salt or ammonium salt, optionally in the presence of a solvent or diluent.

Preferably, $Hal_1$ is chlorine.

If, for example, O-ethyl-N,N-dimethylphosphoric acid ester-amide chloride and 1-(2-cyanoethyl)-3-hydroxy-5-chlorotriazole are used as starting materials, the course of the reaction can be represented by the following formula scheme:

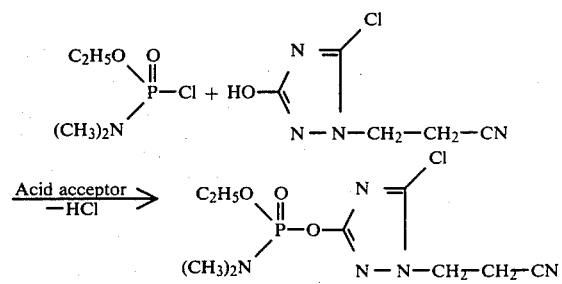

The (thiono)(thiol)-phosphoric(phosphonic) acid ester halides and ester-amide halides (II) are known from the literature and can be prepared in accordance with conventional processes. The following may be mentioned as examples of these compounds: O,O-dimethyl-, O,O-diethyl-, O,O-di-n-propyl-, O,O-di-isopropyl-, O,O-di-n-butyl-, O,O-di-sec.-butyl-, O,O-di-isobutyl-, O,O-di-tert.-butyl-, O-methyl-O-ethyl-, O-ethyl-O-n-propyl-, O-ethyl-O-isopropyl-, O-ethyl-O-tert.-butyl- or O-ethyl-O-sec.-butylphosphoric acid diester chloride and the corresponding thiono analogues, and also O,S-dimethyl-, O,S-diethyl-, O,S-di-n-propyl-, O,S-di-isopropyl-, O,S-di-n-butyl-, O,S-di-isobutyl-, O,S-di-sec.-butyl-, O,S-di-tert.-butyl-, O-methyl-S-ethyl-, O-ethyl-S-n-propyl-, O-ethyl-S-isopropyl-, O-ethyl-S-n-butyl-, O-n-propyl-S-ethyl-, O-n-propyl-S-n-butyl- or O-isopropyl-S-ethyl-thiolphosphoric acid diester chloride and the corresponding thiono compounds, furthermore O-methyl-N-methyl-, O-ethyl-N-ethyl-, O-n-propyl-N-n-propyl-, O-isopropyl-N-isopropyl-, O-n-butyl-N-n-butyl-, O-isobutyl-N-isobutyl-, O-sec.-butyl-N-sec.-butyl-, O-tert.-butyl-N-tert.-butyl-, O-ethyl-N-isopropyl-, O-isopropyl-N-ethyl-, O-tert.-butyl-N-ethyl- or O-sec.-butyl-N-ethyl-phosphoric acid ester-amide chloride and the corresponding thiono compounds and dialkylamino compounds, and further O-methyl-, O-ethyl-, O-n-propyl-, O-isopropyl-, O-n-butyl-, O-isobutyl-, O-sec.-butyl- or O-tert.-butyl-methane-, -ethane-, -n-propane-, -iso-propane-, -n-butane-, -iso-butane-, -sec.-butane-, -tert.-butane- or -phenyl-phosphonic acid ester chloride and the corresponding thiono compounds.

The triazole derivatives of the formula (III) can be prepared in accordance with customary processes, for example by reacting 2-cyanoalkylhydrazine with N-chlorocarbonylisocyanide dichloride in accordance with the following formula scheme:

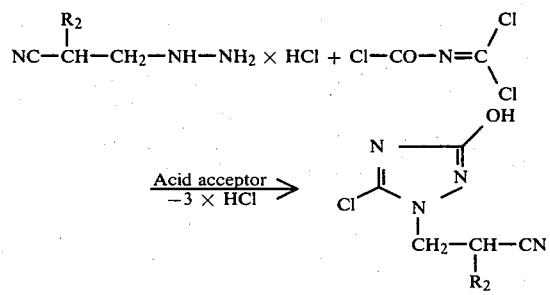

wherein $R_2$ has the above-mentioned meaning.

The following may be mentioned as examples of triazole derivatives (III): 1-(2-cyanoethyl)- and 1-(2-cyanopropyl)-3-hydroxy-5-chlorotriazole.

The process according to the invention is preferably carried out in the presence of a suitable solvent or diluent. Practically all inert organic solvents can be used for this purpose. These include in particular aliphatic and aromatic optionally chlorinated hydrocarbons, for example, benzene, toluene, xylene, benzine, methylene chloride, chloroform, carbon tetrachloride and chlorobenzene; ethers, for example diethyl ether, dibutyl ether and dioxan; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate, methylate and ethylate and potassium carbonate, methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at 0° to 120° C., preferably at 40° to 70° C.

The reaction is in general allowed to take place under normal pressure.

To carry out the process, the starting components are in general employed in equimolar amounts. An excess of one or other reactant does not result in any essential advantages. The reaction is preferably carried out in one of the abovementioned solvents or diluents in the presence of an acid acceptor, with stirring at the stated temperature. After a reaction time of one to several hours, in most cases at an elevated temperature, the reaction mixture may be worked up in accordance with generally customary methods.

In general they are poured into water after having cooled, and taken up in an organic solvent, for example methylene chloride, the organic phase is washed and dried, and the solvent is distilled off, in most cases in vacuo.

The new compounds are obtained in the form of oils which in most cases cannot be distilled without decomposition, but are freed from the last volatile constituents by so-called "slight distillation", that is to say by prolonged heating under reduced pressure to moderately elevated temperatures, and are purified in this way. They are characterized by the refractive index.

As already mentioned repeatedly, the O-triazolyl(thiono)(thiol)-phosphoric(phosphonic) acid esters and ester-amides according to the invention are distinguished by an excellent insecticidal and acaricidal activity. They are not only active against insects and mites which damage plants, but also against hygiene pests and pests of stored products. They combine a low phytotoxicity with a good action against both sucking and biting insects and mites.

For this reason, the compounds according to the invention can be employed successfully as pesticides in plant protection and in the hygiene field and the field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus=Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the compounds of the invention are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following Table 1:

TABLE 1

| (Plutella test) | | |
|---|---|---|
| Active compound | Active compound concentration in % | Degree of destruction in % after 3 days |
| CH₃—N——N, CH₃S on N, S=P(OCH₃)₂ group (known) (A) | 0.1<br>0.01<br>0.001 | 100<br>100<br>0 |
| CH₃(NC)CH—CH₂—N——N, Cl on N, S=P(OC₂H₅)₂ group (7) | 0.1<br>0.01<br>0.001 | 100<br>100<br>100 |

EXAMPLE 2

Doralis test (systemic action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were each watered with 20 ml of the preparation of the active compound so that the preparation penetrated into the soil without wetting the leaves of the bean plants. The active compound was taken up from the soil by the bean plants and thus passed to the infested leaves.

After the specified periods of time, the degree of destruction was determined as a percentage. 100% means that all the aphids were killed; 0% means that none of the aphids were killed.

The active compounds, the concentrations of the active compounds, the evaluation times and the results can be seen from the following Table 2:

TABLE 2

| (Doralis test/systemic) | | |
|---|---|---|
| Active compound | Active compound concentration in % | Degree of destruction after 4 days |
| iso-C₃H₇—N——N, CH₃S on N, S=P(OC₂H₅)(O-phenyl) group | 0.1 | 0 |

TABLE 2-continued (Doralis test/systemic)

| Active compound | Active compound concentration in % | Degree of destruction after 4 days |
|---|---|---|
| (known) (B) | 0.1 | 100 |
| Structure (6): NC—CH$_2$—CH$_2$—N—N, Cl, N, O—P(=S)(CH$_3$)(OC$_3$H$_7$-iso) | 0.1 | 100 |
| Structure (1): NC—CH$_2$—CH$_2$—N—N, Cl, N, O—P(=S)(OC$_2$H$_5$)$_2$ | 0.1 | 100 |
| Structure (2): NC—CH$_2$—CH$_2$—N—N, Cl, N, O—P(=S)(C$_2$H$_5$)(OC$_2$H$_5$) | 0.1 | 100 |
| Structure (4): NC—CH$_2$—CH$_2$—N—N, Cl, N, O—P(=S)(OC$_2$H$_5$)(NH—C$_3$H$_7$-iso) | 0.1 | 100 |
| Structure (7): (CH$_3$)(NC)CH—CH$_2$—N—N, Cl, N, O—P(=S)(OC$_2$H$_5$)$_2$ | 0.1 | 100 |

EXAMPLE 3

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the common or two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following Table 3:

TABLE 3

(Tetranychus test)

| Active compound | Active compound concentration in % | Degree of destruction in % after 2 days |
|---|---|---|
| (CH$_3$)$_2$CH—N—N, Cl, N, O—P(=S)(OC$_2$H$_5$)$_2$ | 0.1 | 99 |
| | 0.01 | 90 |
| | 0.001 | 0 |
| (known) (c) (CH$_3$)(NC)CH—CH$_2$—N—N, Cl, N, O—P(=S)(OC$_2$H$_5$)$_2$ (7) | 0.1 | 100 |
| | 0.01 | 100 |
| | 0.001 | 75 |

EXAMPLE 4

LT$_{100}$ test for Diptera

Test insects: *Aedes aegypti*
Solvent: acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following Table 4:

TABLE 4
(LT₁₀₀ test for Diptera/Aedes aegypti)

| Active compound | Active compound concentration of the solution in % | LT₁₀₀ in minutes (') or hours (hrs) |
|---|---|---|
| CH₃\S\\=N—C₃H₇-iso  N—N  O—P(=S)(—OC₂H₅)(—C₆H₅) (known) (B) | 0.1 | 3 hrs = 70% |
| Cl\\=N—CH₂—CH₂—CN  N—N  O—P(=S)(—OC₂H₅)₂ (1) | 0.2  0.02 | 60'  180' |
| Cl\\=N—CH₂—CH₂—CN  N—N  O—P(=S)(—OC₂H₅)(—C₂H₅) (2) | 0.2  0.02 | 60'  120' |
| Cl\\=N—CH₂—CH₂—CN  N—N  O—P(=S)(—CH₃)(—OC₃H₇-iso) (6) | 0.2  0.02 | 60'  120' |

TABLE 4-continued
(LT₁₀₀ test for Diptera/Aedes aegypti)

| Active compound | Active compound concentration of the solution in % | LT₁₀₀ in minutes (') or hours (hrs) |
|---|---|---|
| 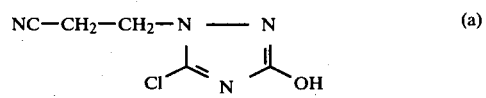 (7) | 0.2  0.02 | 60'  120' |

The following further examples are set forth to illustrate, without limitation, the manner of producing the instant compounds according to the present invention:

EXAMPLE 5

NC—CH₂—CH₂—N———N
            \\      ||
             C      C
            / \\   / \\
           Cl   N    OH                (a)

17 g (0.2 mole) of 2-cyanoethylhydrazine were dissolved in 100 ml of acetonitrile and 7.3 g of hydrogen chloride gas were passed in at −10° C. Thereafter, 32 g of N-chlorocarbonylisocyanide dichloride were added dropwise at 0° C., whilst cooling and stirring well, and after completion of this addition, 30 g of potassium carbonate were added. This mixture was first stirred for 2 hours at room temperature and was then heated under reflux until no further evolution of hydrogen chloride was detectable (5 to 6 hours). After cooling, the mixture was filtered, the residue was washed with acetonitrile and the entire filtrate was concentrated by evaporation in vacuo. The oil which remained was taken up in a little ethanol and cooled to −10° to −15° C. The colorless crystals which had precipitated were filtered off and dried. 20 g of 1-(2-cyanoethyl)-5-chloro-3-hydroxy-1,2,4-triazole of melting point 149°–150° C. were obtained.

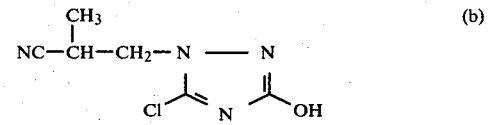

19.8 g (0.2 mole) of 2-cyanopropylhydrazine were dissolved in 150 ml of acetonitrile and 7.3 g of hydrogen chloride gas, dissolved in 50 ml of acetonitrile, were added at 0° C. Thereafter 32 g of N-chlorocarbonylisocyanide dichloride were added dropwise at 0° to 10° C., while cooling, and after completion of this addition 30 g of potassium carbonate were stirred in at 10° C. The mixture was stirred for 2 hours at room temperature and was then heated for 4 to 6 hours under reflux. After cooling, it was filtered and the solvent was stripped off in vacuo. The oil residue was dissolved in a little ethanol and cooled to −15° C. Thereupon, 4.5 g of 1-(2-cyanopropyl)-5-chloro-3-hydroxy-1,2,4-triazole of melting point 166°–168° C. crystallized out.

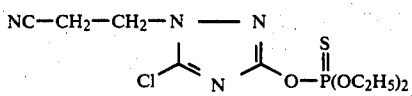

(c)

10 g (0.058 mole) of 1-(2-cyanoethyl)-5-chloro-3-hydroxy-1,2,4-triazole from (a) were dissolved in 150 ml of absolute acetonitrile and heated with 8 g of potassium carbonate under reflux for 1 hour, while stirring. The mixture was then cooled to room temperature, 10.8 g of diethylthionophosphoric acid diester chloride were added dropwise and the whole was warmed to 60° C. for 4 hours, while stirring. After cooling, the reaction mixture was diluted with 500 ml of water and extracted with 200 ml of methylene chloride. The organic phase was separated off and dried over sodium sulfate. After filtering off the drying agent, the methylene chloride was stripped off in vacuo and the residue was briefly subjected to slight distillation at 60° C./2 mm Hg. 10.2 g (54% of theory) of O,O-diethyl-O-[1-(2-cyanoethyl)-5-chloro-1,2,4-triazol(3)yl]-thionophosphoric acid ester were obtained as a light-colored oil of refractive index $n_D^{20}$: 1.4955.

EXAMPLE 6

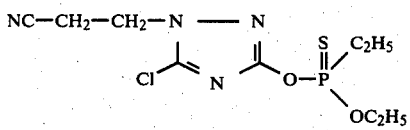

(2)

10.9 g of O-ethylthionoethanephosphonic acid ester chloride were added dropwise, while stirring, to a mixture of 10 g (0.058 mole) of 1-(2-cyanoethyl)-5-chloro-3-hydroxy-1,2,4-triazole from 5(a), 5.8 g of triethylamine and 150 ml of absolute acetonitrile, and the reaction solution was warmed to 60° C. for 45 minutes, cooled, poured into 500 ml of water and extracted with 200 ml of methylene chloride. The organic phase was separated off and dried over sodium sulfate and the solvent was distilled off in vacuo. The soil which remained was briefly subjected to slight distillation at 60° C./2 mm Hg. 13.6 g (71% of theory) of O-ethyl-O-[1-(2-cyanoethyl)-5-chloro-1,2,4-triazol(3)yl]thionoethanephos- phonic acid ester were obtained as a colorless oil of refractive index $n_D^{20}$: 1.5168.

The following compounds of the formula

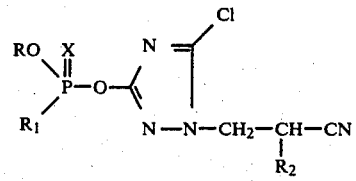

were prepared analogously

TABLE 5

| Compound No. | R | $R_1$ | $R_2$ | X | Physical data (refractive index) | Yield (% of theory) |
| --- | --- | --- | --- | --- | --- | --- |
| 3 | —$C_2H_5$ | —$SC_3H_7$-n | H | S | $n_D^{20}$:1.5337 | 32 |
| 4 | —$C_2H_5$ | —NH—$C_3H_7$-iso | H | S | $n_D^{25}$:1.5031 | 85 |
| 5 | —$C_2H_5$ | —$C_6H_5$ | H | S | $n_D^{20}$:1.5649 | 41 |
| 6 | —$C_3H_7$-iso | —$CH_3$ | H | S | $n_D^{20}$:1.5121 | 78 |
| 7 | —$C_2H_5$ | —$OC_2H_5$ | —$CH_3$ | S | $n_D^{20}$:1.5008 | 40 |
| 8 | —$C_2H_5$ | —$OC_3H_7$-n | H | S | $n_D^{20}$:1.4971 | 51 |
| 9 | —$C_2H_5$ | —$OC_2H_5$ | H | O | $n_D^{20}$:1.4704 | 62 |
| 10 | —$C_2H_5$ | —$OC_3H_7$-n | —$CH_3$ | S | $n_D^{23}$:1.4985 | 48.6 |

Other compounds which can be similarly prepared include

| Compound No. | R | $R_1$ | $R_2$ | Hal | X |
| --- | --- | --- | --- | --- | --- |
| 11 | —$CH_3$ | —$C_3H_7$-iso | —$C_3H_7$-iso | Br | O |
| 12 | —$C_4H_9$-n | —$SCH_3$ | —$C_2H_5$ | F | O |

It will be appreciated that the instant specification and examples are set forth by way of illustration and not limitation, and that various modifications and changes may be made without departing from the spirit and scope of the present invention.

What is claimed is:

1. The compound O,O-diethyl-O-[1-(2-cyanopropyl)-5-chloro-1,2,4-triazol(3)yl]-thionophosphoric ester of the formula

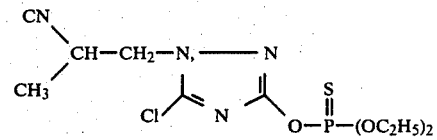

2. An insecticidal or acaricidal composition containing as active ingredient an insecticidally or acaricidally effective amount of a compound according to claim 1 in admixture with a diluent.

3. A method of combating insect or acarid pest which comprises applying to the pests or a habitat thereof an insecticidally or acaricidally effective amount of a compound according to claim 1.

* * * * *